US012329638B2

(12) United States Patent
Krumpelmann et al.

(10) Patent No.: US 12,329,638 B2
(45) Date of Patent: Jun. 17, 2025

(54) ANCHORING DEVICES, SYSTEMS, AND METHODS FOR IMPLANTABLE DEVICE

(71) Applicant: Boston Scientific Scimed, Inc., Maple Grove, MN (US)

(72) Inventors: Graham Krumpelmann, Stillwater, MN (US); Levi Wolterstorff, Saint Paul, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 176 days.

(21) Appl. No.: 17/546,622

(22) Filed: Dec. 9, 2021

(65) Prior Publication Data

US 2022/0183834 A1 Jun. 16, 2022

Related U.S. Application Data

(60) Provisional application No. 63/123,632, filed on Dec. 10, 2020.

(51) Int. Cl.
*A61F 2/24* (2006.01)

(52) U.S. Cl.
CPC .... *A61F 2/2427* (2013.01); *A61F 2220/0016* (2013.01)

(58) Field of Classification Search
CPC ............ A61F 2/2327; A61F 2220/0016; A61F 2/2442; A61F 2/2309; A61F 2/2418; A61F 2/24; A61F 2/2445; A61F 2/2448; A61F 2220/00; A61F 2220/0008; A61F 2/2451; A61F 2/2454; A61F 2/2257; A61F 2/246;

(Continued)

(56) References Cited

U.S. PATENT DOCUMENTS 4,989,617 A 2/1991 Memberg et al.
8,216,302 B2 7/2012 Wilson et al.

(Continued)

FOREIGN PATENT DOCUMENTS

WO 2016047202 A1 3/2016

OTHER PUBLICATIONS

International Search Report and Written Opinion dated Jun. 16, 2022 for International Application No. PCT/US2021/062604.

(Continued)

*Primary Examiner* — Sarah A Long
*Assistant Examiner* — James R McGinnity
(74) *Attorney, Agent, or Firm* — Seager, Tufte & Wickhem, LLP

(57) ABSTRACT

An anchoring system including an anchoring assembly having two or more anchor elements, and anchor drive mechanism having a respective actuator portion couplable with each anchor element and operable to separately and independently actuate each anchor element. In some embodiments, the actuator portions are on different portions of a common actuator component. The actuator portions actuate the anchor elements by different actuation movements. Is some embodiments, the actuator portions use different types of actuation movements, such as rotational motion to actuate one anchor element, and axial motion to actuate another anchor element. The actuator portions may be formed on different portions of a common actuator component, or as different structures coupled together.

17 Claims, 14 Drawing Sheets

1044
1046
1060
1036
1062
1042
1035
1065
1028
1020
1043
1032
1030

(58) Field of Classification Search

CPC .... A61F 2/2463; A61F 2/2466; A61F 2/2487; A61F 2002/249; A61F 2002/0072; A61F 2/0811; A61F 2002/0817; A61F 2002/0829; A61F 2002/0835; A61F 2002/0841; A61B 2017/0649; A61B 2017/0647; A61B 2017/00243; A61B 2017/0409

See application file for complete search history.

(56) References Cited

U.S. PATENT DOCUMENTS

| | | | |
|---|---|---|---|
| 8,506,623 | B2 | 8/2013 | Wilson et al. |
| 9,180,005 | B1 | 11/2015 | Lashinski et al. |
| 9,788,948 | B2 | 10/2017 | Gilmore et al. |
| 10,335,275 | B2 | 7/2019 | Lashinski et al. |
| 10,548,731 | B2 | 2/2020 | Lashinski et al. |
| 2005/0107871 | A1 | 5/2005 | Realyvasquez et al. |
| 2007/0010843 | A1 | 1/2007 | Green |
| 2009/0240326 | A1 | 9/2009 | Wilson et al. |
| 2009/0287304 | A1 | 11/2009 | Dahlgren et al. |
| 2011/0082538 | A1 | 4/2011 | Dahlgren et al. |
| 2011/0093062 | A1 | 4/2011 | Cartledge et al. |
| 2012/0296417 | A1 | 11/2012 | Hill et al. |
| 2013/0268042 | A1* | 10/2013 | Hastings ................ A61N 1/362 607/128 |
| 2016/0015513 | A1 | 1/2016 | Lashinski et al. |
| 2016/0235526 | A1 | 8/2016 | Lashinski et al. |
| 2018/0116645 | A1 | 5/2018 | Nosler |
| 2018/0116800 | A1* | 5/2018 | Alon ..................... A61F 2/2445 |
| 2019/0336288 | A1 | 11/2019 | Gross et al. |
| 2019/0374343 | A1 | 12/2019 | Lashinski et al. |
| 2020/0187919 | A1 | 6/2020 | Long et al. |
| 2020/0289265 | A1* | 9/2020 | Gifford, III ........... A61F 2/2418 |
| 2020/0297489 | A1* | 9/2020 | Bishop ............... A61B 17/0487 |
| 2021/0161664 | A1 | 6/2021 | Krumpelmann et al. |

OTHER PUBLICATIONS

International Search Report and Written Opinion dated Mar. 24, 2022 for International Application No. PCT/US2021/050196.

* cited by examiner

ANCHORING DEVICES, SYSTEMS, AND METHODS FOR IMPLANTABLE DEVICE

PRIORITY

The present application is a non-provisional of, and claims the benefit of priority under 35 U.S.C. § 119 to, U.S. Provisional Application Ser. No. 63/123,632, filed Dec. 10, 2020, the disclosure of which is hereby incorporated herein by reference in its entirety for all purposes.

FIELD

The present disclosure relates generally to anchoring systems configured to anchor medical devices to tissue, and associated devices, such as deployment devices, and methods. In particular, the present disclosure relates to improvements to anchoring of implantable medical devices, such as implantable medical devices for repair or reconstruction of heart anatomy, and associated devices, systems, and methods.

BACKGROUND

Various medical devices are implanted into soft tissue for temporary or permanent therapy or treatment. Such devices include annuloplasty devices configured to reshape or reconfigure a heart valve annulus to restore proper functioning of the heart, such as to repair mitral insufficiency which may allow mitral regurgitation. One challenge presented by implanting devices into soft tissue (such as cardiac tissue and muscle) is anchoring and fixing the device for long periods without anchor migration or pullout. A further difficulty with devices implanted in the heart is that the heart is constantly beating and thus is in constant motion. To ensure implant effectiveness, it is important that the integrity of the anchoring mechanism used to secure the implant to the valve annulus is able to accommodate the stresses and strains experienced by the implant as a result of chronic palpatory forces. Devices and systems and methods which may reinforce or strengthen the positioning or connection of an implantable device in an implant site, and/or reduce migration (shifting or loosening) of the implantable device with respect to the treatment site, and/or reduce potential tissue damage at the treatment site (such as when the implantable device is manipulated, such as cinched, to modify the valve annulus configuration, or later after the procedure has been completed) would be welcome. Additionally, there is a need for various implantable devices to comply with various space constraints generally presented by delivery routes as well as the implant site.

It is with considerations of these and other challenges in mind that improvements such as disclosed herein may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with one general aspect, the present disclosure is directed to an anchor assembly including a first anchor element, a second anchor element, and an anchor drive mechanism, wherein the anchor assembly is configured to be mounted on an implantable device. In some aspects, the anchor drive mechanism includes a first actuator portion configured to engage the first anchor element, and a second actuator portion configured to engage the second anchor element, the first actuator portion and the second actuator portion separately and independently moving the first anchor element and the second anchor element.

In various embodiments, the first actuator portion and the second actuator portion respectively move the first anchor element and the second anchor element by different actuation movements. In some embodiments, the first actuator portion rotationally moves the first anchor element. In some embodiments, the second actuator portion axially moves the second anchor element. In some embodiments, the first actuator portion is axially movable relative to the second anchor element, such as when moving the first anchor element rotationally. In some embodiments, the second actuator portion is rotationally movable relative to the first anchor element, such as when moving the second anchor element axially. In some embodiments, the second actuator portion is rotationally movable relative to the second anchor element. In some embodiments, the first actuator portion is axially movable relative to the second actuator portion. In some embodiments, the anchor drive mechanism is configured to move either of the first anchor element or the second anchor element either distally or proximally.

In various embodiments, the first anchor element is a rotatably advanced helical anchor and the second anchor element is an axially advanced talon anchor.

In various embodiments, the first actuator portion and the second actuator portion are formed on different portions of an anchor cover.

In various embodiments, the first actuator portion is coupled to and axially movable relative to the second actuator portion.

In accordance with another general aspect, the present disclosure is directed to an implantable device including a frame; an anchor assembly mounted on the frame; and an anchor drive mechanism. In some embodiments, the anchor assembly includes a first anchor element and a second anchor element; and the anchor drive mechanism includes a first actuator portion configured to engage the first anchor element and a second actuator portion configured to engage the second anchor element. In some embodiments, the first actuator portion and the second actuator portion separately and independently move the first anchor element and the second anchor element.

In some embodiments, the first actuator portion and the second actuator portion respectively move the first anchor element and the second anchor element by different actuation movements.

In some embodiments, the first actuator portion and the second actuator portion are formed on different portions of an anchor cover.

In some embodiments, the first actuator portion is coupled to and axially movable relative to the second actuator portion.

In accordance with yet another general aspect, the present disclosure is directed to a method of securing an anchor assembly to tissue, the method including: engaging a first actuator portion of an anchor drive mechanism with a first anchor element of an anchor assembly; engaging a second actuator portion of the anchor drive mechanism with a second anchor element of the anchor assembly; actuating the first actuator portion to move the first anchor element without moving the second anchor element; and actuating the second actuator portion to move the second anchor element without moving the first anchor element.

In some embodiments, actuating the first actuator portion includes rotating the first actuator portion to rotate the first anchor element without axially moving the second anchor element; and actuating the second actuator portion includes axially moving the second actuator portion to axially move the second anchor element without rotating the first anchor element.

In some embodiments, the first actuator portion and the second actuator portion are formed on different portions of a common actuator component, the method further including: selectively engaging the first actuator portion with the first anchor element to move the first anchor element; disengaging the first actuator portion from the first anchor element and engaging the second actuator portion with the second anchor element to move the second anchor element relative to the first anchor element.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
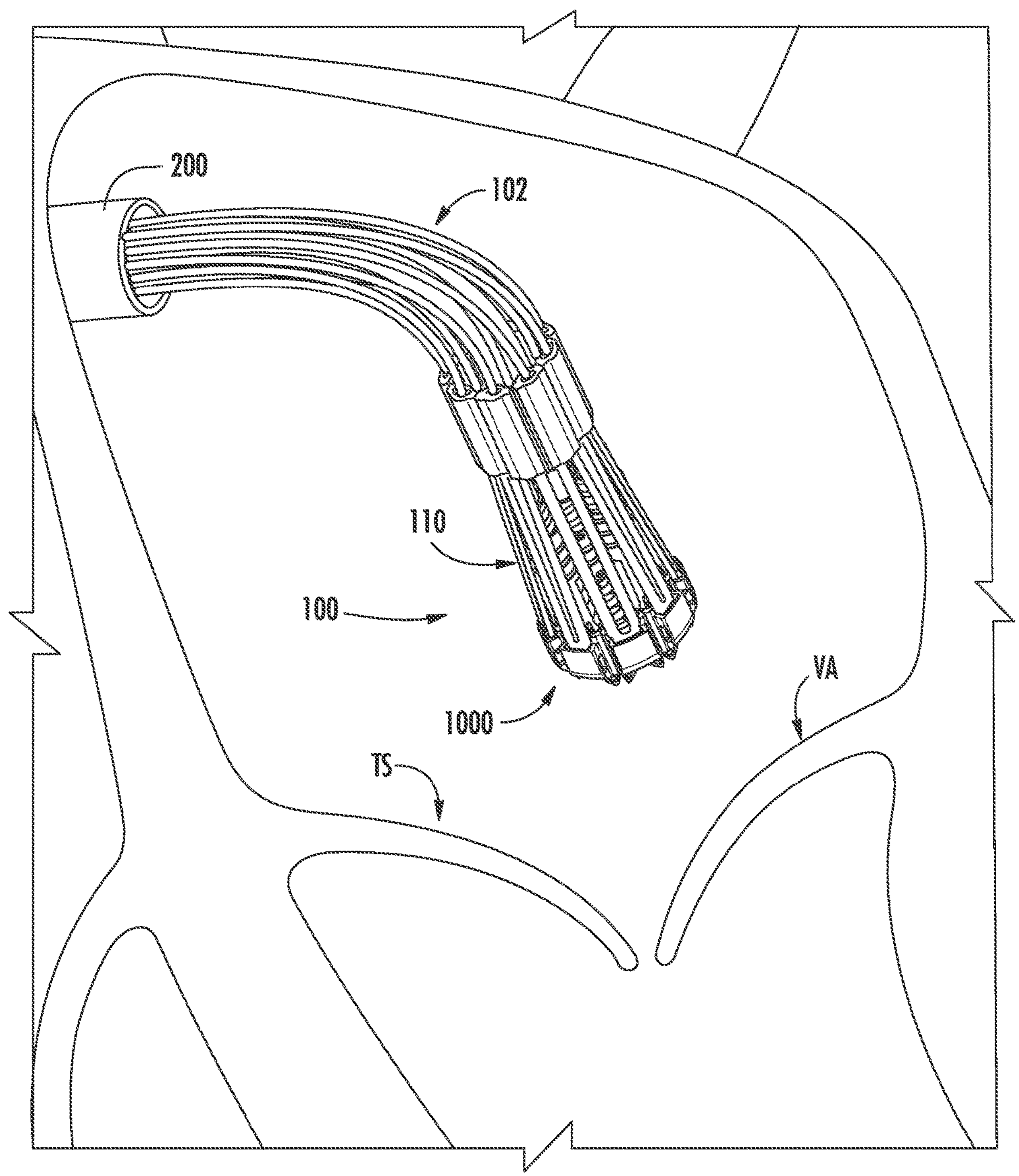
FIG. 1 is a schematic view of a human heart valve with an example of an implantable device with anchoring and deployment systems formed in accordance with various aspects of the present disclosure, the implantable device shown in a compact delivery configuration for delivery to the implant site.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or systems and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element.

Various principles of the present disclosure may be applied broadly to various elements, devices, apparatuses, mechanisms, etc. implanted in the body. It will be appreciated that terms such as implant may be used interchangeably herein with terms such as affix, secure, couple, engage, anchor, hold etc., without intent to limit. Whereas various implantable devices generally do not have more than one type of anchoring element, in accordance with various principles of the present disclosure, an implantable device is provided with two or more different types of anchoring elements at a common site or location on the device. More particularly, in accordance with various principles of the present disclosure, an implantable device is provided with an anchor system comprising at least one anchor assembly coupled to the implantable device to secure the implantable device with tissue at a desired treatment site (which may alternately referenced as an implant site or site of implantation or the like, without intent to limit). The anchor assembly includes two or more types of anchor elements, preferably configured to engage the treatment site in different manners, such as to increase efficacy of the retention strength and/or pull-out strength of the anchor assembly, such as by improving retention of the implantable device at the treatment site by distributing retention forces in different manners. It will be appreciated that the term anchor element is used for the sake of convenience and may be used interchangeably herein with terms such as anchor, anchor device, anchor mechanism, anchor component, anchoring element, anchoring device, anchoring mechanism, anchoring component, and the like, such terms being known in the art to represent structures configured to hold another object in place. In one embodiment, the anchor assembly includes a first axially-extending anchor, such as a helical anchor having a helical element, such as a coil, to hold the anchor in place, and a second anchor element that distributes forces differently (e.g., radially). In one embodiment, the anchor assembly includes a talon anchor as a second anchor element. A talon anchor may include one or more tines held in a substantially linear configuration along a longitudinal axis of the anchor assembly until deployed, whereupon one or more of the tines may be deflected away from the longitudinal axis to be driven laterally/radially into tissue, thereby increasing the resistive surface area of the anchor.

The anchor elements of an anchor assembly of the present disclosure may also differ by being actuated in different manners. For instance, a helical anchor generally is advanced into the implant site by rotation thereof. In contrast, a talon anchor generally is advanced, at least initially, axially. In some embodiments, the talon anchor is advanced axially, whereupon the tines may deflect or curve (e.g., extend radially outwardly) so that the distal ends of the tines deflect away from a central anchoring axis as the tines are deployed. Such deflection may be due to the resilient nature of the tine, through mechanical manipulation of the tine, or a combination thereof.

In accordance with various aspects of the present disclosure, an anchor system with an anchor assembly having multiple anchor elements (providing two or more anchors at a common location on the implantable device) is provided with an actuator system (with one or more actuators) which operatively engages respective anchors to move the anchors into engagement with the implantation site. It will be appreciated that the term actuator is used herein for the sake of convenience and may be used interchangeably herein with such terms as driver or pusher or controller (with or without the term "mechanism") or drive mechanism or control mechanism or the like without intent to limit. It will further be appreciated that the term move may be used interchangeably herein with such terms as advance, retract, manipulate, actuate, deploy, drive, implant, etc., in various forms or conjugations thereof, without intent to limit. In some embodiments, the actuators separately and/or independently engage the one or more anchors to separately and/or independently move the anchors. Because different anchors may use different actuation techniques or movements or motions (e.g., rotational actuation movements or axial actuation movements relative to the frame on which the anchors are mounted), the actuators may be configured to achieve actuation and implantation of anchors by different types of engagements and/or movements and/or motions. In some embodiments, the actuator(s) has a proximal end outside the patient in which the implantable device is implanted, or is coupled to another element extending outside the patient, so that the actuator(s) is accessible by a medical professional to control each anchor element separately and independently. The anchor assembly may include additional components such as components configured to couple anchors of the anchor assembly with an associated actuator, and/or components configured to mount the anchors on an implantable device and with respect to each other. It will be appreciated that terms such as coupling and mounting may be used interchangeably herein with other terms such as interacting or engaging or the like, and various forms and conjugations thereof, without intent to limit.

Various space constraints, such as during delivery (e.g., through narrow passages in the body) as well as at the implantation site itself, affect not only the implantable device and associated anchor assemblies, but also the anchor actuators. Accordingly, anchors and actuators of an anchor system formed in accordance with various principles of the present disclosure may be configured to be compact. In some embodiments, the anchors are mounted or otherwise configured in the anchor assembly to minimize space occupied by the anchors. For instance, the anchors may be mounted substantially coaxially. In addition, or alternatively, in some embodiments, the actuators are mounted or otherwise configured to minimize space occupied by the actuators. For instance, the actuators may be mounted substantially coaxially. In some embodiments, the same actuator is used to selectively engage both of the anchor elements separately and/or independently, to actuate each anchor element separately and/or independently. In some embodiments, the same actuator actuates each of the two or more anchor elements. For instance, the actuator may include a first actuator structure (such as at a first portion of the actuator) configured to engage and actuate a first anchor, and a second actuator structure (such as at a second portion of the actuator, which may be adjacent or spaced apart from the first portion) configured to engage and actuate a second anchor. In some embodiments, the first actuator structure and the second actuator structure are formed on different portions of a common actuator component. In some embodiments, the first and second actuator structures are formed separately and coupled together at a distal end of the actuator to move in conjunction with each other (the proximal end of the actuator may remain a common element accessible proximally by a medical professional). In some embodiments, the actuator actuates each of the two or more anchor elements by different actuation movements, such as by rotational motion to actuate one anchor element, and by axial motion to actuate another anchor element, or the same type of motion (e.g., rotational or axial) performed separately (e.g., a first rotational motion and a second rotational motion, or a first axial motion and a second axial motion). The actuator may be engaged with the first anchor element to actuate the first anchor element while being engaged with the second anchor element yet not actuating the second anchor element. The actuator may be engaged with the second anchor element to actuate the second anchor element while being engaged with the first anchor element yet not actuating the first anchor element. Alternatively the actuator may be disengaged from the first anchor element when actuating the second anchor element. The actuator may be engaged with both the first anchor element and the second anchor element when actuating one of the first or second anchor elements, and then disengaged from the one of the first or second anchor elements to actuate the other of the first or second anchor elements.

A particular environment which may benefit from the use of more than one type of anchoring element at a common location, such as a coiled anchor as well as a talon anchor or barbs, is the heart. Heart muscle and valve annulus tissue have different characteristics, and the forces or loads on various implantable devices or mechanisms implanted in or on the heart differ depending on the type of tissue in which the device or mechanism is implanted as well as the type of device or mechanism being implanted. For instance, an implantable device for annuloplasty, such as for custom reshaping of a heart valve (e.g., a mitral valve or tricuspid valve) actively manipulates and/or changes the shape or structure of a heart valve annulus, and therefore generally has greater loads than a pacer mechanism which transmits electrical current without reshaping tissue structure. To ensure implant effectiveness, it is important that the integrity of the anchoring mechanism used to secure the implant to the valve annulus is able to accommodate the stresses and strains experienced by the implant as a result of chronic palpatory forces, and to remain securely engaged with the heart tissue to maintain the repair device in place and to maintain the desired configuration of the heart structure. Additionally, an implantable annuloplasty device has a greater likelihood of fatiguing tissue at the implantation site than a device, such as a pacer, which predominantly functions to hold in place a device with very little additional load applied by the device.

Because a heart valve annulus has a configuration (e.g., wall thickness, curvature, etc.) which varies along the heart valve, the present disclosure provides alternate anchor elements which may be selectively separately and independently implanted into the tissue, including to different depths, depending on the characteristics of the tissue, thereby improving retention of the implantable device. For instance, anchoring forces may be better distributed over a greater surface area of the cardiac tissue using two different types of anchor elements at a common anchoring assembly location on the implantable device, or different anchor elements or combinations thereof at different locations along the implantable device. The anchor assembly and associated anchor actuators of the present disclosure, and associated devices and systems, may be configured to be delivered in a minimally invasive manner, such as endoluminally, and percutaneously such as transfemorally, transeptally, or transapically.

In one embodiment, the implantable device is an annuloplasty device comprising a frame in the form of a generally tubular frame with a proximal end and a distal end. Two or more anchor elements extend distally from a distal end of the frame, and are advanceable into the heart tissue. In some embodiments, the frame is formed of a plurality of struts, adjacent struts forming a proximal apex at a proximal end of the frame and a distal apex at the distal end of the frame. Two or more anchoring devices or mechanism formed in accordance with principles of the present disclosure may be provided on one or more distal apices to anchor the implantable device with respect to tissue. The anchor elements may be provided as part of an anchoring assembly provided at at least one distal apex of the frame. The anchor assembly is configured to carry and/or to facilitate deployment of the one or more anchor elements at the at least one distal apex.

Although embodiments of the present disclosure may be described with specific reference to mitral valves, principles of the present disclosure are also applicable to tricuspid valves, and beyond implantable annuloplasty devices in general.

Various embodiments of anchoring systems providing an anchor assembly with more than one type of anchor element and corresponding anchor actuators for the one or more anchor elements will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, it will be appreciated that in the following description, elements or components similar among the various illustrated embodiments are generally designated with the same reference numbers increased by 100, or a multiple thereof, and redundant description is omitted. Common features are identified by common reference elements and, for the sake of brevity, the descriptions of the common features are generally not repeated. For purposes of clarity, not all components having the same reference number are numbered.

Figure 2:
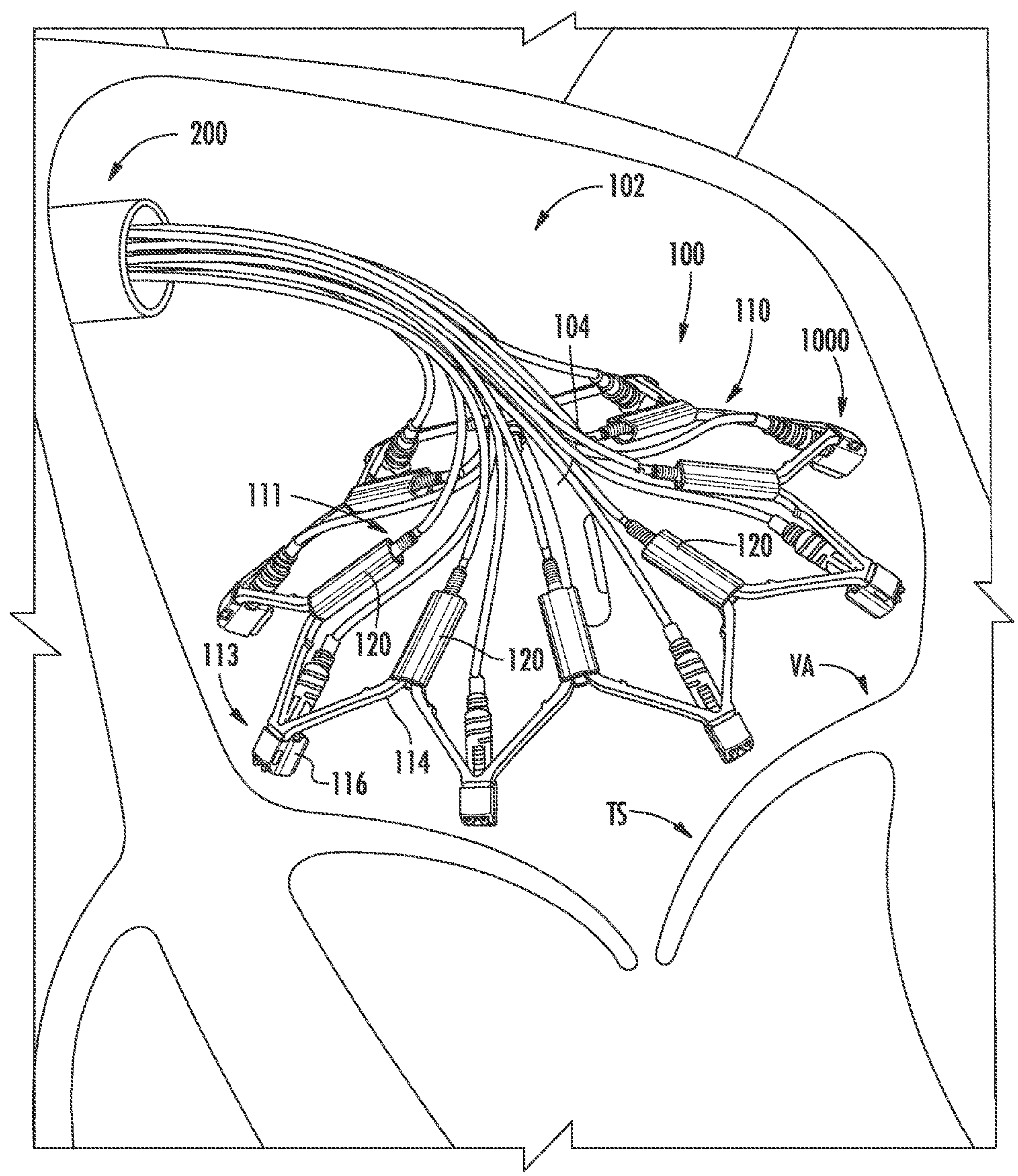
FIG. 2 is a view similar to that of FIG. 1, but with the implantable device in an expanded configuration in preparation for being implanted in the valve annulus using an anchor system formed in accordance with various aspects of the present disclosure.

Generally, it is desirable for implant and delivery systems to be able to be placed in a compact (e.g., collapsed or compressed or simply unexpanded) configuration for delivery, and to be expanded (self-expanded or expanded with assistance of another device or system) once delivered to the treatment site or site at which the implantable device is to be implanted. An example of an implantable device 100 which may benefit from an anchor assembly 1010 formed in accordance with principles of the present disclosure is an implantable annuloplasty device, for custom reshaping of a heart valve (e.g., the mitral valve, as illustrated, or the tricuspid valve), such as illustrated in FIGS. 1 and 2. The implantable device 100 may be configured to be delivered in a minimally invasive manner in a compact (e.g., collapsed or compressed or simply unexpanded) configuration, such as sized to fit within a delivery sheath or catheter 200 for delivery to the heart, such as illustrated in FIG. 1. The implantable device 100 may be expanded into an operable unexpanded configuration, as illustrated in FIG. 2, once delivered to a heart valve annulus. The implantable device 100 may expand naturally (e.g., may be self-expandable), for example if the frame is formed of a shape memory or superelastic material (e.g., Nitinol) that is biased towards an expanded state, or with assistance of an expansion device or mechanism, for example through the use of a force applied within the frame such as using an expandable deployment device (e.g., an inflatable balloon or the like). Once delivered, the implantable device 100 is deployed and secured to the heart at the implantation site, such as with a tissue anchor system 1000 as described herein. The shape, size, dimension, configuration, etc. of the implantable device 100 may then be adjusted to configure the shape and/or structure of the heart valve annulus VA to which the implantable device 100 is secured, as medically indicated.

An imaging catheter 104 may be used to locate the treatment site TS at which the implantable device 100 is to be delivered/deployed and implanted and/or to observe the configuration and/or position of the implantable device 100 during implantation and adjustment. An example of a steerable delivery device and system with various positioning and imaging capabilities is described in U.S. Pat. No. 10,335,275, titled *Methods For Deployment Of Heart Valve Devices Using Intravascular Ultrasound Imaging,* and issued on Jul. 2, 2019, which patent is incorporated herein by reference in its entirety for all purposes.

Figure 3:
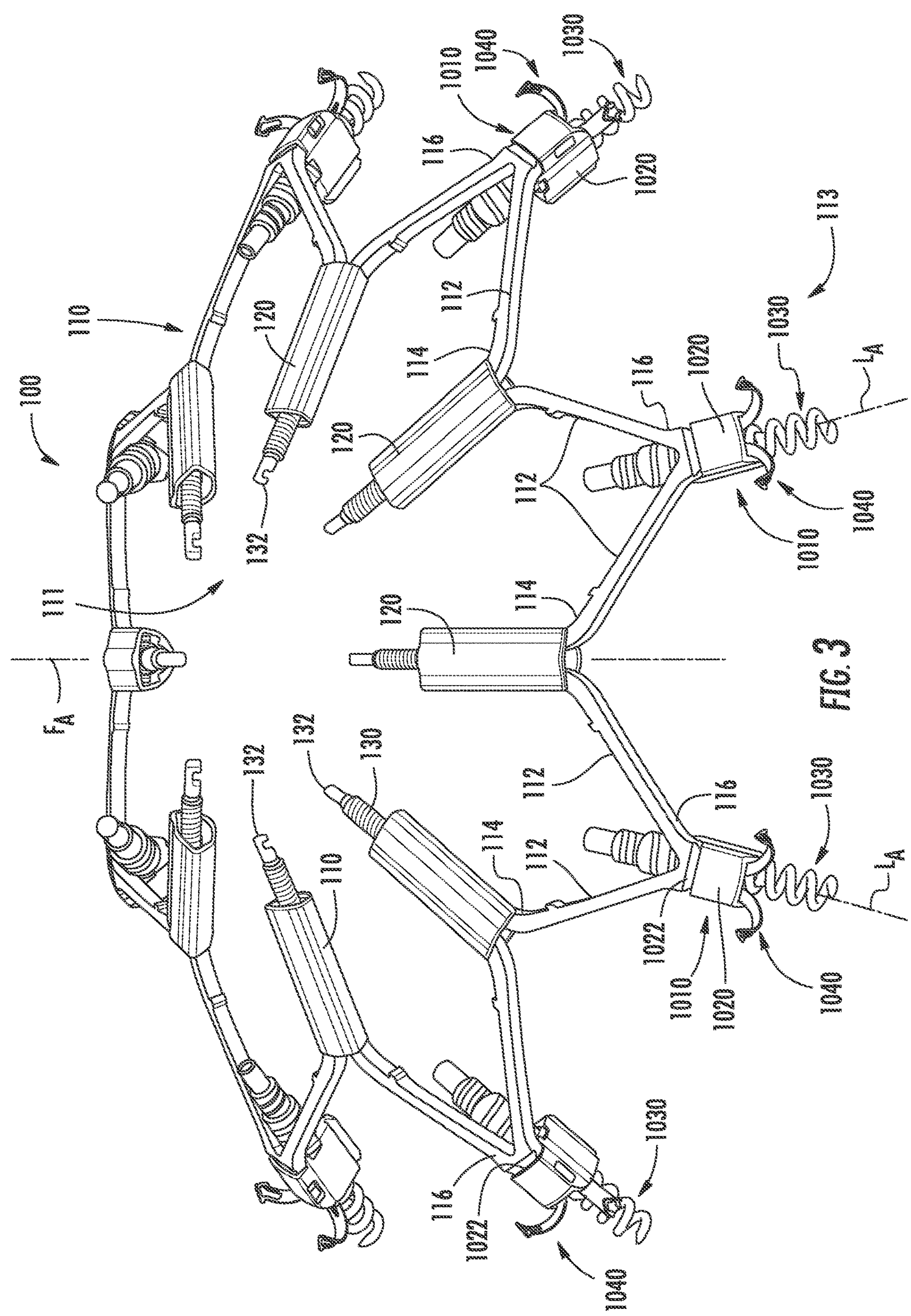
FIG. 3 is a perspective view of a heart valve implant device with an example of an anchor assembly formed in accordance with various principles of the present disclosure and shown in a deployed configuration.

The example of an implantable device 100 illustrated in FIGS. 1 and 2 is illustrated in greater detail in FIG. 3. The implantable device 100 includes a frame member 110 that may be disposed about a heart valve or other cardiac feature, as illustrated in FIG. 2. The frame member 110 may be generally symmetrical with respect to the central frame axis FA although it need not be symmetrical. The frame member 110 may form a generally tubular shape, the term "tubular" being understood herein to include circular as well as other rounded or otherwise closed shapes. The frame member 110 may assume various shapes, sizes, dimensions, configurations, etc. during different phases of deployment such as during pre-delivery, delivery, tissue engagement, anchoring, adjustment (e.g., cinching), etc. For example, the frame member 110 may be configured to change shape, size, dimension, and/or configuration, such as to modify the shape, size, dimension, configuration, etc. of the valve annulus (or other structure) to which it is coupled.

The frame member 110 may be formed from one or more struts 112 that may form all or part of the frame member 110. The struts 112 may include elongated structural members formed of a metal alloy, a shape memory material, such as an alloy of nickel titanium or other metals, metal alloys, plastics, polymers, composites, other suitable materials, or combinations thereof. In one embodiment, the struts 112 may be formed from the same, monolithic piece of material (e.g., tube stock). Thus, reference to struts 112 may refer to different portions of the same, coextensive component. Alternatively, reference to struts 112 may refer to components that are formed separately and attached together (optionally permanently, such as by welding or soldering or other methods). In some embodiments, the struts 112 may be separate components that are detachably coupled to form proximal apices 114 and distal apices 116. Alternatively, if formed from a monolithic piece of material, the material may be cut or otherwise formed to define proximal apices 114 and distal apices 116. In the illustrated embodiments, the proximal end 111 of the frame member 110 is directed proximally toward and engaged or carried by the delivery/deployment system 102, and the distal end 113 of the frame member 110 extends distally from the delivery/deployment system 102 and is the end engaged with the treatment site TS. It will be appreciated that alternate configurations of the frame member 110, such as depending on the manner and orientation in which the implantable device 100 is delivered, are within the scope and spirit of the present disclosure.

The example of an implantable device illustrated in the figures may be considered to use collar-based adjustment mechanisms, such as a collar-based frame adjusting mechanism and a collar-based anchor housing assembly.

As shown in FIG. 3, in the illustrated example of an embodiment of an implantable device 100, a plurality of cinch collars 120 (such term being used for the sake of convenience, without intent to limit, and may be used interchangeably herein with terms such as collars or sleeves or cinch sleeves or sliders or nuts) are carried at the proximal end 111 of the frame member 110 such as along the proximal apices 114 of the frame member 110, and a plurality of anchor assemblies 1010 are carried at a distal end 113 of the frame member 110, such as along the distal apices 116 of the frame member 110. Advancement or withdrawal of a collar 120 with respect to the proximal apex 114 over which the collar 120 is positioned adjusts the relative positions of the struts 112 joined at such apex. Each collar 120 preferably is adjustable independently of the other collars 120. Such adjustment results in adjustment of at least one of the size, shape, configuration, dimension, etc., of the frame member 110 (e.g., retraction/compression or expansion of the frame upon bringing adjacent struts 112 closer or further apart, respectively) to affect at least one of the size, shape, configuration, dimension, etc., of the treatment site TS (such as to restore or correct the shape of a valve annulus for proper functioning or competency thereof). The collars 120 may be adjusted in various manners, such as by engagement with a threaded collar actuator 130 engaging threads within the collars 120, rotation of the collar actuator 130 (held against axial movement) causing axial movement of the collars 120. A latch 132 may be provided on the collar actuator 130 for engagement by a latch of an actuator provided to actuate (e.g., move, advance, retract, etc.) the collar 120 as desired.

To facilitate anchoring of the implantable device 100 at the treatment site TS, one or more anchor assemblies 1010 are provided, such as along the distal end 113 of the frame member 110 of the implantable device 100. In accordance with various principles of the present disclosure, at least one of the anchor assemblies 1010 illustrated in FIGS. 1-3 includes an anchor assembly 1010 (the term "assembly" being used herein for the sake of convenience, and may be used interchangeably herein with terms such as mechanism or system or the like without intent to limit) which may be a collar-based anchor assembly including an anchor housing 1020 such as in the form of a collar or sleeve or the like. The anchor housing 1020 is configured to be mounted on or to the implantable device 100. In one embodiment, the anchor housing 1020 includes a frame slot 1022 (such term being used for the sake of convenience, without intent to limit, and may be used interchangeably herein with terms such as frame channel, frame sleeve, or the like) configured to receive a portion of the frame member 110, such as a distal apex 116 thereof.

The anchor assembly 1010 further includes two or more anchor elements of different configurations, such as two or more anchors which may distribute forces applied by the implantable device 100 in different manners or directions. For instance, one of the two or more anchor elements may extend axially (e.g., extending distally away from the device in an axial direction, along a longitudinal axis LA of the anchor assembly 1010, when in a deployed configuration as shown), such as a helical anchor 1030 (e.g., a coil-shaped anchor or other configuration generally advanced or retracted by rotation of the anchor). The other of the two or more anchors may extend radially (e.g., with tines or barbs extending radially outwardly from the longitudinal axis LA of the anchor assembly 1010 when in a deployed configuration as shown), such as a talon anchor 1040 (e.g., an anchor element which includes an element such as a talon or tine extending therefrom). It will be appreciated that other configurations and/or combinations of anchor elements are within the scope and spirit of the present disclosure.

Figure 4:
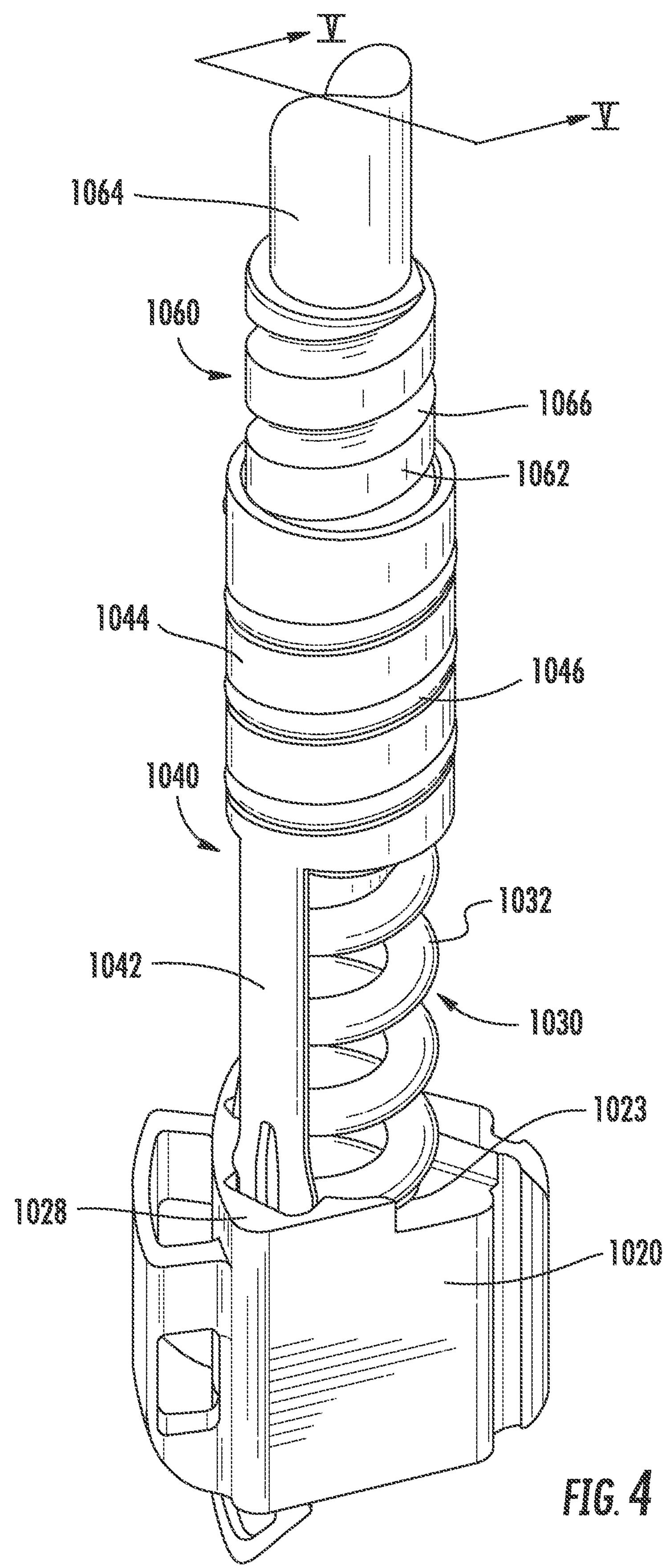
FIG. 4 is a perspective view of an embodiment of an anchor assembly formed in accordance with various aspects of the present disclosure.
Figure 5:
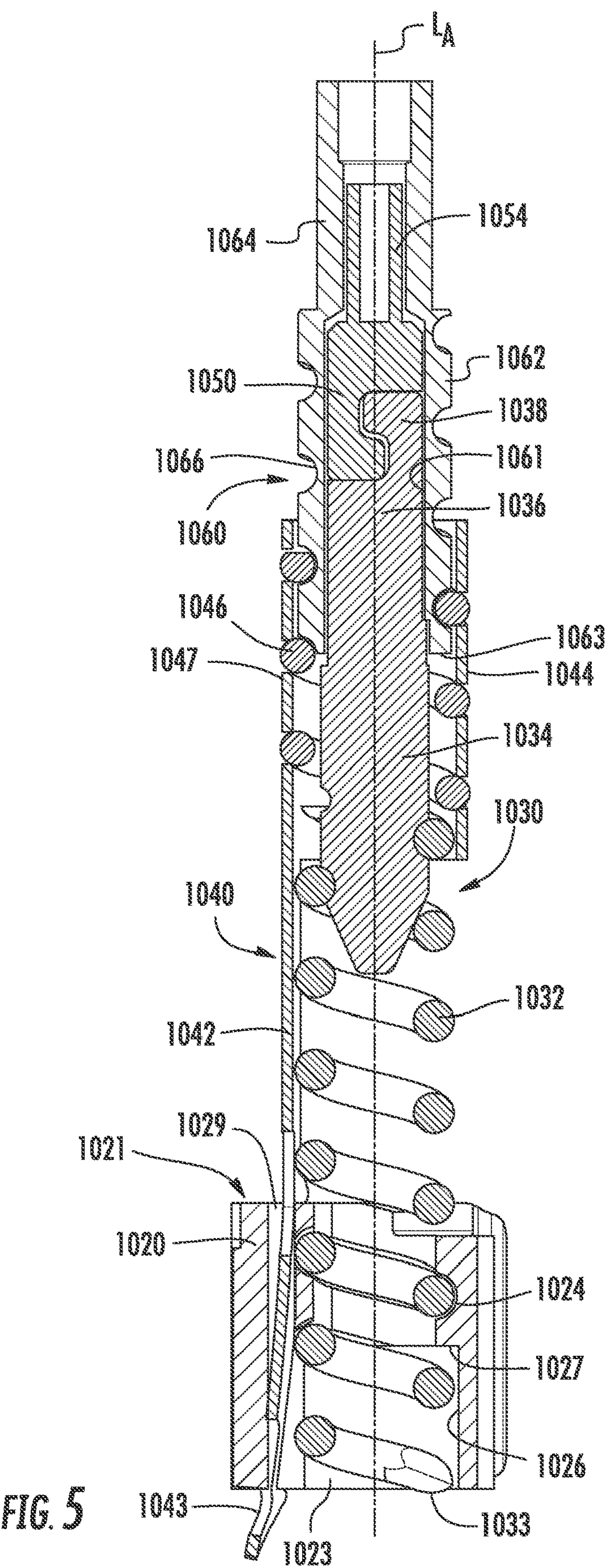
FIG. 5 is a cross-sectional view along line V-V of the anchor assembly of FIG. 4.

In some embodiments, such as the example illustrated in FIG. 4 and FIG. 5, a helical anchor 1030 includes a distal helical coil 1032 coupled to a proximal anchor shaft 1034. The distal end 1033 of the helical coil 1032 may have a sharpened distal tip to facilitate entry and advancement into tissue. The proximal end of the anchor shaft 1034 includes an anchor head 1036 which may be provided with a coupler 1038 configured to engage with an anchor latch 1050 controllable at a proximal end by the medical professional implanting the implantable device 100 to hold the helical anchor 1030 in place during delivery to the treatment site TS. For instance, the anchor latch 1050 may be provided at a distal end of a flexible elongate member 1054 (e.g., hypotube or wire or the like) with a proximal end of the flexible elongate member 1054 extending proximally to a location outside the patient, and, optionally, to a control handle or delivery system handle or the like. In the embodiment illustrated in FIG. 4, as may be appreciated with reference to the cross-sectional view thereof (along line V-V) illustrated in FIG. 5, the helical anchor 1030 passes through an anchor bore 1023 defined through (e.g., axially through) the anchor housing 1020. In some embodiments, mating threads or grooves 1024 are provided in the anchor bore 1023 to guide the helical anchor 1030 as it rotationally advances or retracts through the anchor bore 1023. The anchor bore 1023 may include an unthreaded distal section 1026 in which the coils of the helical anchor 1030 may be positioned when the helical anchor 1030 is substantially fully deployed to allow for "free spin" of the anchor, as described in further detail below.

In some embodiments, the additional anchor included in the anchor assembly 1010 is a talon anchor 1040 such as the example illustrated in FIG. 4 and FIG. 5. The talon anchor 1040 includes one or more tines 1042 extending distally from a talon collar 1044. The tines 1042 and talon collar 1044 are formed from a single tubular element, or as separate elements joined together (such as by welding or soldering or other methods). The tines 1042 may extend distally and axially into tissue at the treatment site TS, and may additionally extend radially away from the longitudinal axis LA of the anchor assembly 1010. The talon anchor 1040 may thus provide an additional direction of engagement of the implantable device 100 with the treatment site TS, such as to enhance securement of the implantable device 100 to the treatment site TS, and optionally also, or alternatively, to permit different directional forces or force vectors to be applied by the anchor assembly 1010. The deflected configuration of the tines 1042 (as illustrated, for example in FIG. 3 and in FIG. 6D) enables the talon anchor 1040 to leverage the resistive force of the tissue to secure the anchor assembly 1010 to the tissue to implant the implantable device 100. In one embodiment, the tines 1042 may be formed from a shape memory material, such as a shape memory alloy (SMA) or similar materials, with the ability to recover a pre-defined configuration. Such materials include, but are not limited to, Nickel Titanium, Graphene, Nitinol, copper-aluminum-nickel, and the like. In one embodiment, the tines 1042 may be biased towards a pre-defined configuration with at least a portion of the tines 1042 deflected away from a longitudinal axis LA of the anchor assembly 1010. For example, in the example illustrated in FIG. 6D, the tines 1042 are shown to be biased in a radially-outward curved configuration, with the distal ends 1043 of the tines 1042 deflected away from the longitudinal axis LA of the anchor assembly 1010. The distal ends 1043 of the tines 1042 may be beveled or otherwise sharpened or pointed to enable the tines 1042 to readily pass through (e.g., to cut through) tissue. With such an arrangement, as the tines 1042 are driven into tissue, the surface area of anchored tissue spans between the distal ends 1043 of the tines 1042, improving retention of the implantable device 100.

Figure 6A:
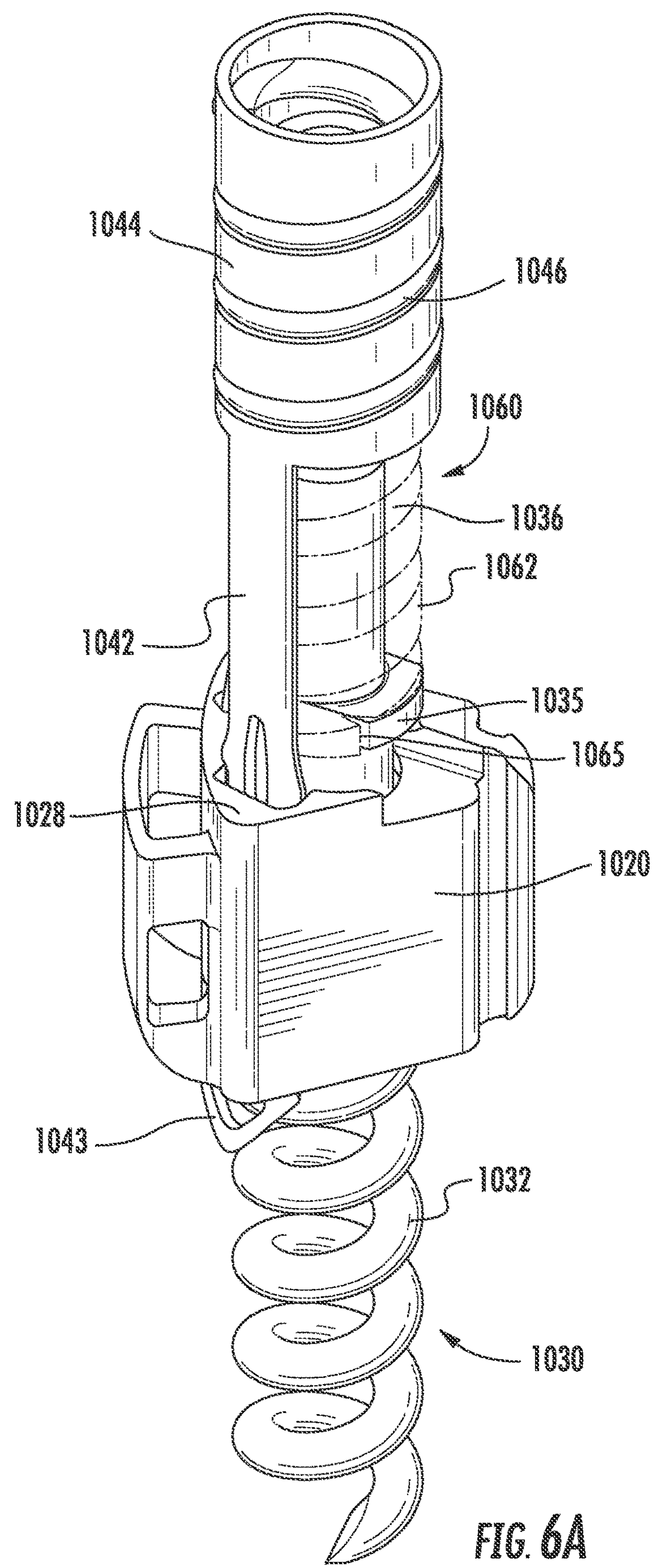
FIG. 6A is a perspective view similar to FIG. 4, but with the helical anchor element being advanced.
Figure 6B:
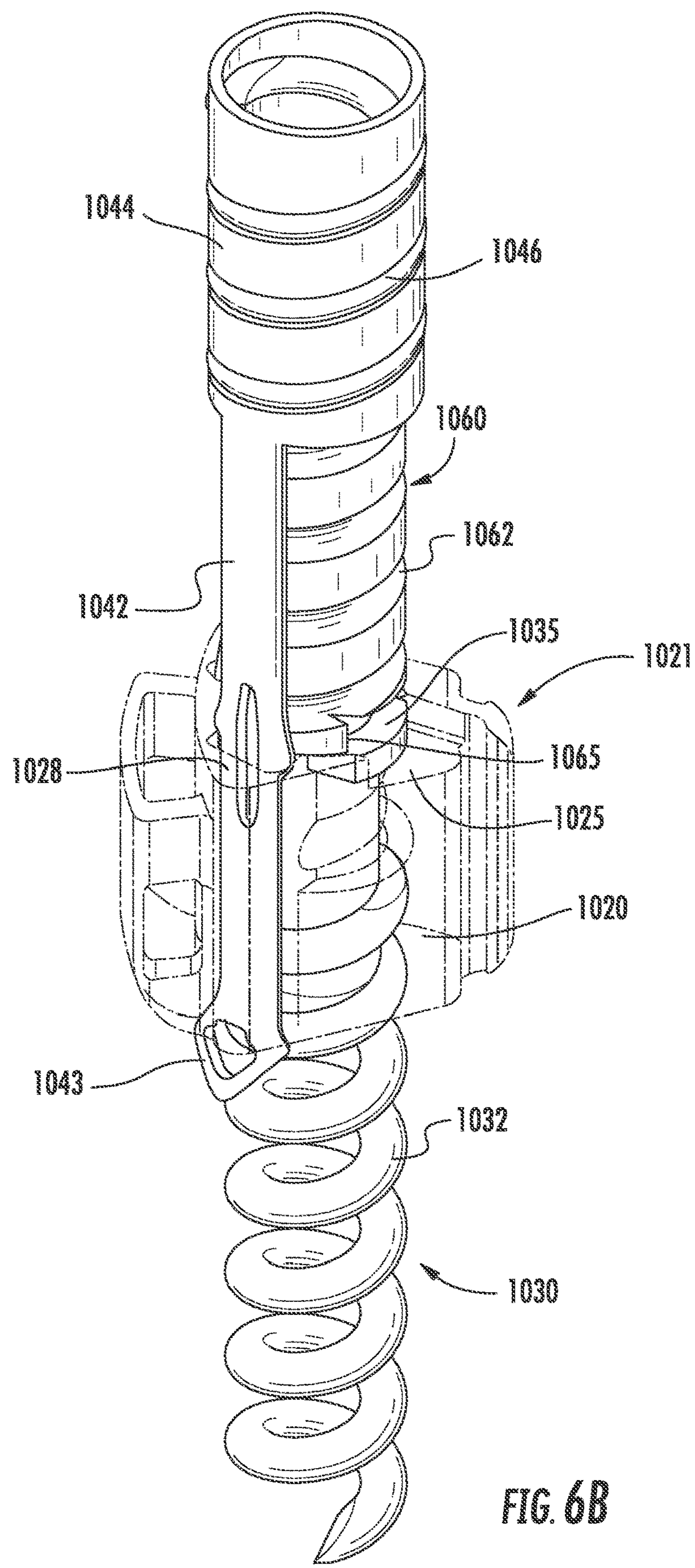
FIG. 6B is a perspective view similar to FIGS. 4 and 6A, but with the helical anchor disengaged from the anchor driver.

Before implantation into tissue, such as illustrated in FIG. 6A and FIG. 6B, the tines 1042 of the talon anchor 1040 may be held in a substantially straight configuration within tine sleeves 1028 of the anchor housing 1020. The distal ends 1043 of the tines 1042 preferably are held within the tine channels 1029 (FIG. 5) defined within the tine sleeves 1028 so as not to extend distally outside the anchor housing 1020 until the appropriate time for deployment of the talon anchor 1040 (such as by being moved or pushed in a generally axial direction). The tines 1042 are slidable through the tine sleeves 1028 to advance therefrom and into tissue at the treatment site TS. In general, the position and number of the tine sleeves 1028 are matched in configuration to the position and number of tines 1042 of the talon anchor 1040. Other talon anchor embodiments that include one, three, or more tines 1042 passing through corresponding tine sleeves 1028 of an anchor housing 1020 are within the scope and spirit of the present disclosure.

In accordance with various principles of the present disclosure, a tissue anchor system 1000 formed in accordance with various principles of the present disclosure may be provided on an implantable device 100 which may be transported transluminally, such as through the patient's vasculature system, and typically within a tubular delivery device (e.g., catheter or sheath or the like). In such case, the tissue anchor systems 1000 must be designed with significant space constraints given the small size of the passages through which the tissue anchor systems 1000 are to be transported. For instance, the implantable device 100 may be transported in a delivery sheath 200 with a limited inner diameter size, typically approximately 0.365" (9.271 mm) in cardiac environments. It will be appreciated that the exact dimension of the tissue anchor systems 1000 will depend on factors such as the number of tissue anchor systems 1000 and other components (e.g., other anchors) provided. Typically, a tissue anchor system 1000 formed in accordance with various principles of the present disclosure for implantation in the heart is dimensioned to fit in an annular sector with an outer radius of approximately 0.14" (3.56 mm) and an inner radius of approximately 0.054" (1.37 cm) and angle of approximately 45 (wherein such dimensions can be a bit flexible if the design is asymmetric). Moreover, access to the device, once at the treatment site, is generally restricted. Accordingly, adjustments must be achievable despite limited accessibility to the components of the implantable device 100 and the tissue anchor systems 1000.

In accordance with an aspect of the present disclosure, an anchor drive mechanism 1060 (such term being used for the sake of convenience, without intent to limit, and may be used interchangeably herein with terms such as actuator system and alternatives thereto without intent to limit) is configured with more than one actuator structure, each actuator structure configured to selectively drive a different one of the two or more anchors of the anchor assembly 1010 into tissue separately and/or independently. In some embodiments, the actuator structures are configured to actuate the different anchors by different types of movement (e.g., axial vs. rotational motion).

In the embodiment illustrated in FIGS. 4, 5, and 6A-6D, the anchor drive mechanism 1060 incorporates a first actuator portion configured to engage and to move (e.g., into or out of tissue) a first anchor element by a first actuation movement (such as rotational motion) as well as second actuator portion configured to engage and to move (e.g., into or out of tissue) a second anchor element by a second actuation movement which may be a different type of movement from the first actuation movement (such as an axial motion compared to a rotational motion). It will be appreciated that the first and second actuation movements may be separate/different movements yet a similar type of movement (in other words, both axial motions or both rotational motions, yet different as applied to different anchor elements). The first actuator portion and the second actuator portion may be configured and arranged to selectively engage the two or more anchors of the anchor assembly 1010 separately and/or independently, and/or to drive the two or more anchors of the anchor assembly 1010 into tissue separately and/or independently. The first actuator portion may be configured to engage and to actuate a rotatable anchor, such as a helical anchor 1030, and may be referenced as an anchor driver (such term being used for the sake of convenience, without intent to limit, and may be used interchangeably herein with terms such as driver, anchor actuator, actuator, anchor cover, etc.). The second actuator portion may be configured to engage and to actuate an axially advanceable anchor, such as a talon anchor 1040, and may be referenced as a talon pusher (such term being used for the sake of convenience, without intent to limit, and may be used interchangeably herein with terms such as pusher, talon driver, driver, talon actuator, actuator, etc.).

In various embodiments disclosed herein, the anchors of the anchor assembly 1010 are advanced into tissue in different manners, such as different types of motions/movements (e.g., rotational or axial or lateral or radial motion/movement). Accordingly, the anchor drive mechanism 1060 may selectively drive the two or more anchors of the anchor assembly 1010, such as a helical anchor 1030 and a talon anchor 1040, separately, such as by different movements of the anchor drive mechanism 1060. However, in some embodiments, a similar motion of the anchor drive mechanism 1060 may be used to advance or retract the two or more anchors. For instance, rotational movement may rotationally and axially advance a helical anchor, and may also advance a non-rotationally axially-advanced anchor (such as a talon anchor), such as by engagement with a threaded element of the non-rotationally axially-advanced anchor (e.g., a threaded collar thereof) such that rotation of the anchor drive mechanism 1060 causes axial advancement of the axially-advanced anchor.

An example of a manner in which the embodiment of an anchor drive mechanism 1060 illustrated in FIGS. 4 and 5 actuates the two or more anchors of the anchor assembly 1010 may be appreciated with reference to FIGS. 6A-6D. The anchor drive mechanism 1060 may include a flexible elongate member 1064 (e.g., a drive tube or the like) with an anchor cover 1062 provided at a distal end thereof. The proximal end of the flexible elongate member 1064 may extend proximally to a location outside the patient, and, optionally, to a control handle or delivery system handle or the like by which the flexible elongate member 1064 may be controlled to control the anchor cover 1062. It will be appreciated that the term control may be used interchangeably herein with such terms as actuate, rotate, move, manipulate, maneuver, etc., without intent to limit. The anchor drive mechanism 1060 may thereby be controlled by the medical professional delivery and/or deploying the implantable device 100 carrying the anchor assembly 1010.

Turning now to FIG. 6A, the anchor drive mechanism 1060 includes an anchor cover 1062 (shown in phantom) which extends over the anchor head 1036 of the helical anchor 1030 to receive the anchor head 1036 in an anchor-receiving bore 1061 (shown in FIG. 5) within the anchor cover 1062. The anchor cover 1062 may cover and hold the anchor latch 1050 and coupler 1038 (described above) in engagement. The anchor cover 1062 and the anchor head 1036 (at least a portion of the anchor shaft 1034) are shaped and configured to be selectively rotationally coupled to rotate together. In the illustrated embodiment, the anchor cover 1062 has a seat 1065 (e.g., a cut-out or groove) and the anchor shaft 1034 has a projection 1035 which extends or seats within the anchor cover seat 1065 to inhibit or prevent relative rotation between the anchor cover 1062 and anchor shaft 1034. It will be appreciated that the reverse configuration, or other configurations which hold the anchor cover 1062 and the anchor shaft 1034 in non-rotatable engagement are within the scope and spirit of the present disclosure. With the anchor cover 1062 and anchor shaft 1034 engaged to rotate together, the anchor cover 1062 may be rotated to drive the helical anchor 1030 distally into the tissue at the treatment site TS to anchor the implantable device 100 thereto.

As may be appreciated with reference to FIG. 5 and FIG. 6A, the talon collar 1044 and the anchor cover 1062 portion of the anchor drive mechanism 1060 include mating threads and grooves. For instance, in the illustrated embodiment the talon collar 1044 includes a helical coil 1046 seated (optionally fixedly seated such as welded or soldered or otherwise thereto or therein) in a helical cutout 1045 (e.g., slit or slot) in the talon collar 1044 to form internal threads (the radially-inward portion of the helical coil 1046 extending through the helical cutout 1047) which mate with and extend within a helical groove 1066 on the anchor cover 1062 to allow relative rotation therebetween. It will be appreciated that the reverse configuration (the helical coil 1046 being mounted on the exterior of the anchor cover 1062 and engaging an interior helical groove within the talon collar 1044) as well as other configurations are within the scope and spirit of the present disclosure. When the anchor cover 1062 is positioned within the talon collar 1044, the anchor cover 1062 is rotatable relative to the talon collar 1044 (which is held against rotation by the tines 1042 being held within the tine sleeves 1028 in the anchor housing 1020) and does not axially advance the talon anchor 1040. While the helical coil 1032 of the helical anchor 1030 extends within the threads 1024 of the anchor bore 1023 of the anchor housing 1020, unintended axial movement of the helical anchor 1030 may be inhibited or prevented, thereby inhibiting or preventing unintended axial advancement of the anchor drive mechanism 1060 when the anchor cover 1062 is engaged with (e.g., threadedly positioned within) the talon collar 1044 and also coupled to the helical anchor 1030, thereby in turn inhibiting or preventing unintended axial movement of the talon anchor 1040.

The helical anchor 1030 may be distally advanced into the tissue until the proximal-most coil of the helical coil 1032 is positioned within the unthreaded distal section 1026 in the anchor bore 1023, such as shown in FIG. 6B (with the anchor housing 1020 shown in phantom). Because the helical coil 1032 is not engaged with the threads 1024 in the anchor bore 1023, further rotation of the helical anchor 1030 does not result in further distal advancement of the helical anchor 1030, but may result in tissue being drawn proximally towards the anchor housing 1020 to improve affixation of the anchor assembly 1010 to the tissue. The proximal-most thread on the helical coil 1032 of the helical anchor 1030 is distal to the threads 1024 in the anchor bore 1023 such that a shoulder 1027 at a distal end of the threads 1024 prevents proximal axial movement of helical coil 1032 with respect to the anchor housing 1020.

As illustrated in FIG. 6B, the helical anchor 1030 may be advanced until the projection 1035 on the anchor shaft 1034 contacts a proximal end 1021 of the anchor housing 1020 and thus cannot be extended further distally. In the illustrated embodiment, the projection 1035 on the anchor shaft 1034 is transferred from the anchor cover seat 1065 and into a seat 1025 in the proximal end 1021 of the anchor housing 1020 to inhibit or prevent further rotational movement of the helical anchor 1030. In some embodiments, the anchor latch 1050 and the anchor drive mechanism 1060 are coupled together to inhibit relative axial movement therebetween as the anchor drive mechanism 1060 moves the helical anchor 1030. In such embodiments, such coupling is released to allow the projection 1035 to be moved out of engagement with the anchor cover seat 1065 and into engagement with the anchor housing seat 1025.

Figure 6C:
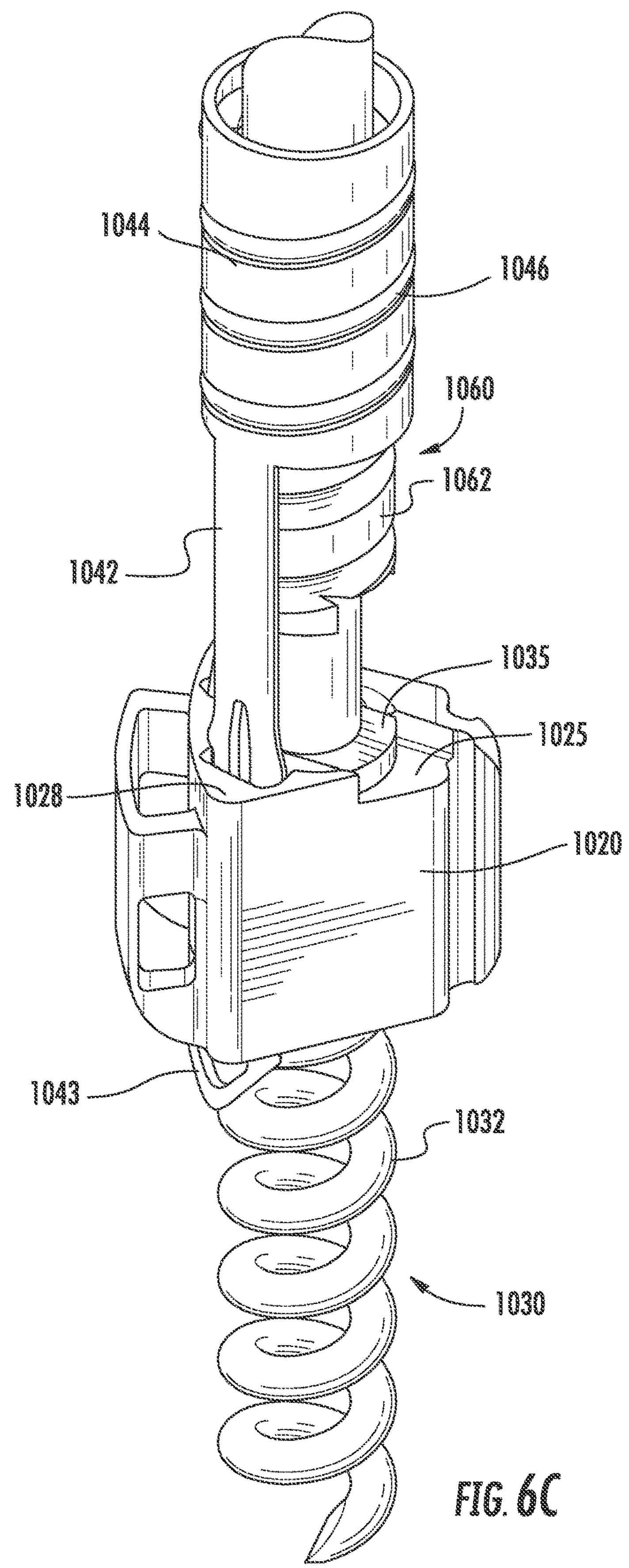
FIG. 6C is a perspective view similar to FIGS. 4, 6A, and 6B, but with the anchor driver engaging the talon anchor to actuate the talon anchor.
Figure 6D:
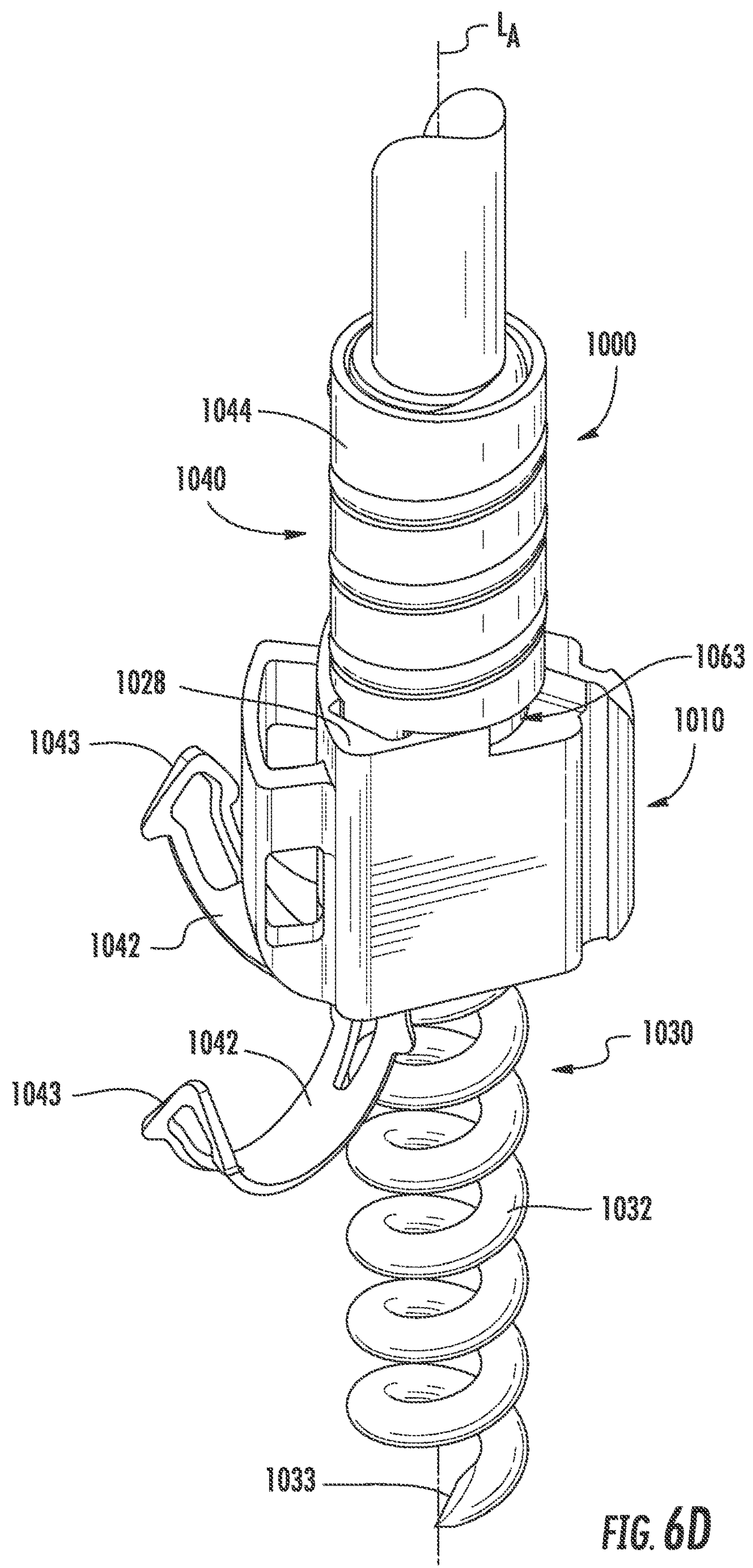
FIG. 6D is a perspective view similar to FIGS. 3, 6A, 6B, and 6C, but with the talon anchor deployed.

In the embodiment illustrated in FIG. 6B, once the helical anchor 1030 has been advanced as far as desired, the anchor cover 1062 may be positioned distal to the talon collar 1044 such that the mating threads and grooves of the anchor cover 1062 and the talon collar 1044 are disengaged. The helical anchor 1030 may be rotated in the reverse direction to backthread into the talon collar 1044, as illustrated in FIG. 6C, to engage the talon collar 1044 so that the anchor drive mechanism 1060 may now be used to actuate the talon anchor 1040 to be implanted into the tissue. Initially, once the anchor drive mechanism 1060 is operatively engaged with the talon anchor 1040 (such as by operative engagement of the anchor cover 1062 with the talon collar 1044), the anchor drive mechanism 1060 may be axially advanced in a distal direction to advance the tines 1042 of the talon anchor 1040 distally to the desired extent. Once the distal end 1063 of the anchor cover 1062 engages the proximal end 1021 of the anchor housing 1020, the anchor cover 1062 cannot be further extended distally, and further advancement of the tines 1042 (if not already fully advanced) may be achieved by rotating the anchor cover 1062 to drive the talon collar 1044 (which is fixed against rotating) distally to secure the talon anchor 1040 in the tissue as desired. In the embodiment illustrated in FIG. 6D, the tines 1042 curve radially outwardly from the longitudinal axis LA of the anchor assembly 1010.

The anchor cover 1062 may be rotated in the reverse direction again to disengage from the talon collar 1044. The anchor drive mechanism 1060 may be withdrawn axially from the anchor assembly 1010 in the proximal direction to deploy the anchor assembly 1010 and implantable device 100 at the treatment site TS. The implantable device 100 may be adjusted, as desired, such as described above, to effect the desired treatment.

It will be appreciated that the above movements may be performed in a reverse order to adjust or remove the anchor assembly 1010 and optionally also the implantable device 100.

Moreover, it will be appreciated that various modification may be made to various elements or parts of the anchor assembly 1010 and/or the anchor drive mechanism 1060 without departing from the various broad principles of the present disclosure.

Figure 7:
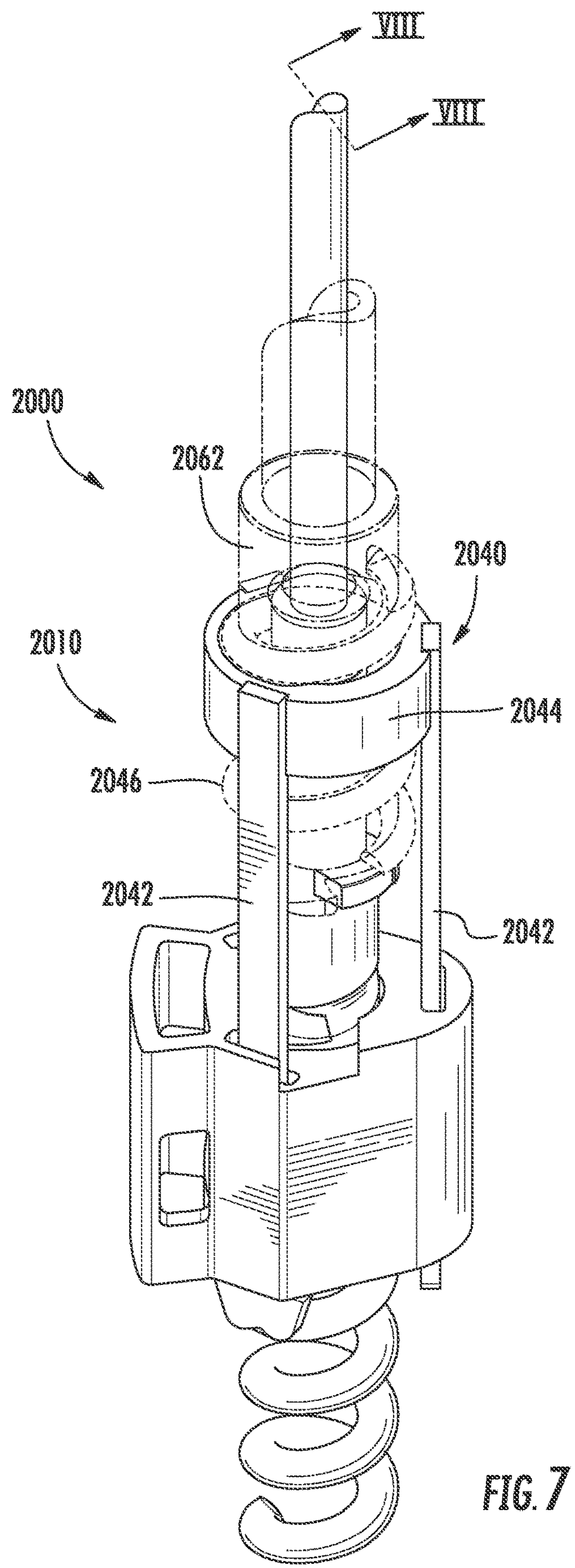
FIG. 7 is a perspective view of another embodiment of an anchor assembly formed in accordance with various aspects of the present disclosure.
Figure 8:
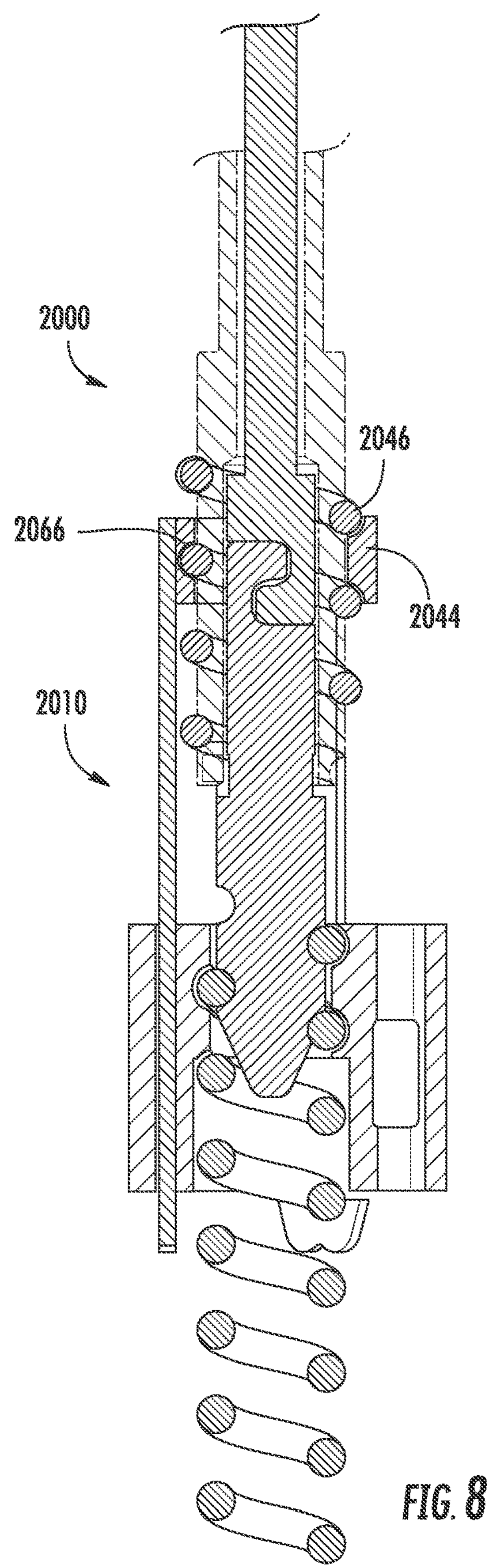
FIG. 8 is a cross-sectional view along line VIII-VIII of the anchor assembly of FIG. 7.

For instance, various modifications may be made to the anchor cover 1062 and talon collar 1044 beyond those described above. An example of a further modification is illustrated in FIG. 7, in which an anchor assembly 2010 includes a talon anchor 2040 having a talon collar 2044 differing from the talon collar 1044 of the embodiment of FIGS. 4 and 5 in one or more manners. For instance, the talon collar 2044 may be formed separately from the tines 2042, with the two elements coupled together such as by welding, soldering, brazing, crimping, or other methods. Additionally or alternatively, the talon collar 2044 of the embodiment of FIGS. 7 and 8 may have a shorter extent than the talon collar 1044 in the above-described embodiments of FIGS. 4 and 5. Additionally or alternatively, the engagement of the talon collar 2044 and anchor cover 2062 of the embodiment of FIGS. 7 and 8 may be substantially the reverse of the configuration in the embodiment of FIGS. 4 and 5. In particular, as may be appreciated with reference to FIG. 8 (illustrating a cross-sectional view along line VIII-VIII in FIG. 7), the talon collar 2044 is provided with an internal groove or threads receiving external threads on an anchor cover 2062 of the anchor drive mechanism 2060. The external threads on the anchor cover 2062 may be formed in a traditional manner as known to those in the art, or as a separate coil fitted and coupled within a cutout, with an outwardly-extending portion of the coil forming exterior threads (similar to the threads on the talon collar 1044 of FIGS. 4 and 5). For instance, a helical coil 2046 may be provided on the anchor cover 2062 to engage an internal helical groove 2066 within the talon collar 2044. As in the embodiment of FIGS. 4 and 5, the helical coil 2046 in the embodiment of FIGS. 7 and 8 may be separately formed and afterwards coupled to (e.g., by welding or soldering or other methods) the anchor cover 2062. The operation of the tissue anchor system 2000 of the embodiment illustrated in FIGS. 7 and 8 is substantially the same as the operation of the embodiment illustrated in FIGS. 4 and 5, as described with reference to FIGS. 6A-6F. Accordingly, reference is made to the operations described with respect to FIGS. 6A-6F for a description of the operation of the embodiment of FIGS. 7 and 8 and, for the sake of brevity, not repeated herein.

Figure 9:
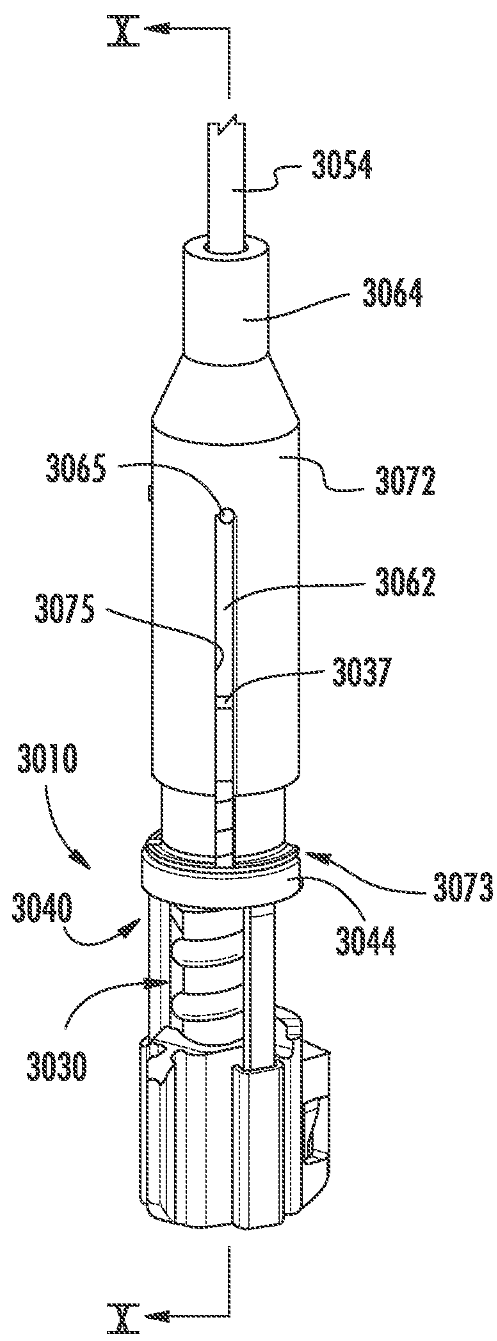
FIG. 9 is a perspective view of another embodiment of an anchor assembly formed in accordance with various aspects of the present disclosure.
Figure 10:
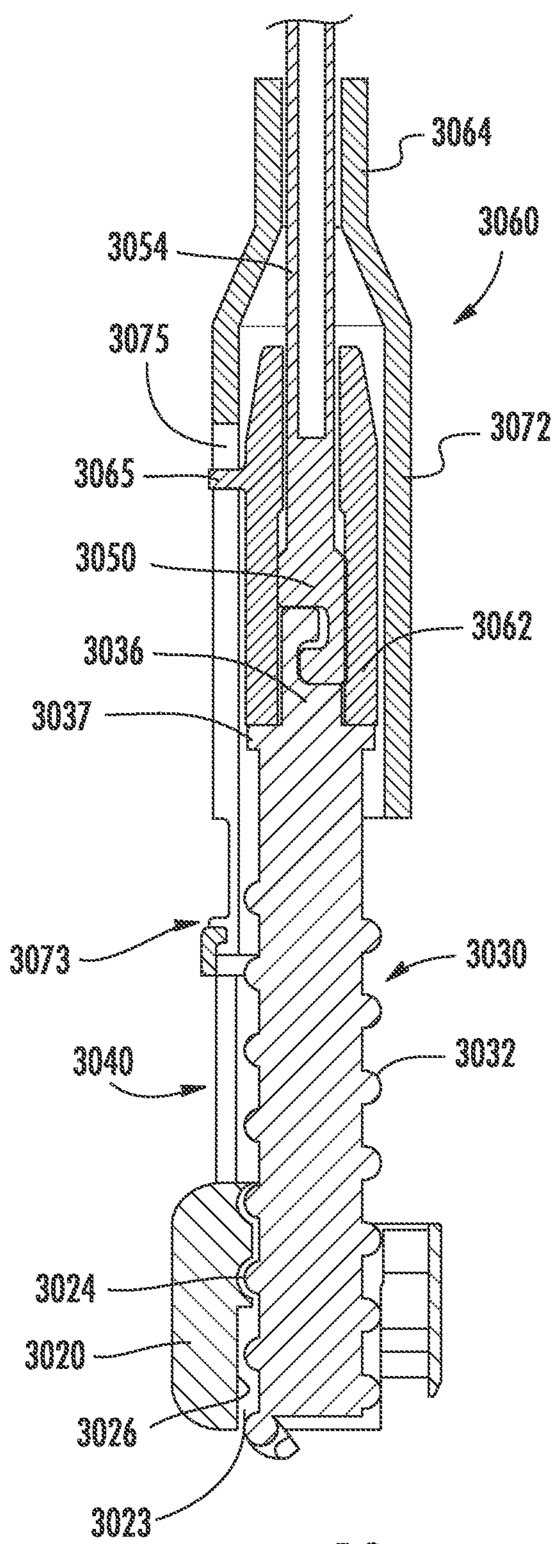
FIG. 10 is a cross-sectional view along line X-X of the anchor assembly of FIG. 9.

In accordance with further principles of the present disclosure, the first actuator portion and the second actuator portion of an anchor drive mechanism 3060 may be formed as separately movable components, such as an anchor cover 3062 separate from a talon pusher 3072, as illustrated in FIGS. 9 and 10 performing different actuation movements to actuate the respective associated anchor elements. As may be appreciated with reference to the cross-sectional view of FIG. 10 (along line X-X of FIG. 9), the anchor cover 3062 extends over the anchor head 3036 of a helical anchor 3030 of the anchor assembly 3010 to cover the anchor head 3036 and an anchor latch 3050 (which may be provided at a distal end of a hypotube 1054 having a proximal end accessible for controlling the hypotube 3054 and anchor latch 3050 as described above with reference to the embodiment of FIGS. 4 and 5). The anchor cover 3062 and the anchor head 3036 may be shaped and configured to be rotationally coupled together such that rotation of the anchor cover 3062 rotates the anchor head 3036. For instance, the anchor cover 3062 and anchor head 3036 may have non-circular matching shapes, or a detent-recess interlocking configuration, or other interconnection inhibiting or preventing relative rotational movement therebetween. Additionally, the anchor cover 3062 is shaped and configured to be rotationally coupled with the talon pusher 3072 such the talon pusher 3072 and the anchor cover 3062 rotate together while allowing relative axial movement therebetween (for reasons which will be described in further detail below). In the illustrated embodiment, the anchor cover 3062 includes a projection 3065 extending through an axial slot 3075 (such term being used for the sake of convenience, without intent to limit, and may be used interchangeably herein with terms such recess or groove or the like) in the talon pusher 3072. However, other configurations allowing relative axial movement and inhibiting relative rotational movement between the anchor cover 3062 and the talon pusher 3072 (such as non-circular matching shapes) are within the scope of the present disclosure. In the illustrated embodiment, the anchor cover 3062 is substantially coaxially mounted within the talon pusher 3072. However, other arrangements are within the scope and spirit of the present disclosure. The talon pusher 3072 may be provided at a distal end of a flexible elongate member 3064 (e.g., a drive tube or the like) with a proximal end of the flexible elongate member 3064 extending proximally to a location outside the patient, and, optionally, to a control handle or delivery system handle or the like. Rotation or other movement of the flexible elongate member 3064 rotates or otherwise moves the talon pusher 3072 and the anchor cover 3062 which is rotationally coupled therewith. The talon pusher 3072 is engaged with the talon collar 3044 of the talon anchor 3040 of the anchor assembly 3010 in a manner which allows relative rotation therebetween while allowing axial movement of the talon pusher 3072 to effect axial movement of the talon anchor 3040. For instance, the distal end 3073 of the talon pusher 3072 may be provided with a circumferential ridge or groove 3077 engaging a corresponding groove or ridge 3047 on the talon collar 3044, as illustrated, for example, in FIG. 11C. It will be appreciated that various modifications to configurations of the corresponding ridges and grooves, such as relative positions (e.g., on interior vs. exterior sides) or shapes, and/or other manners of engagement between the talon pusher 3072 and talon collar 3044 (such as allowing the talon pusher 3072 and the talon collar 1044 to move together axially yet rotate relative to each other) are within the scope and spirit of the present disclosure.

Figure 11A:
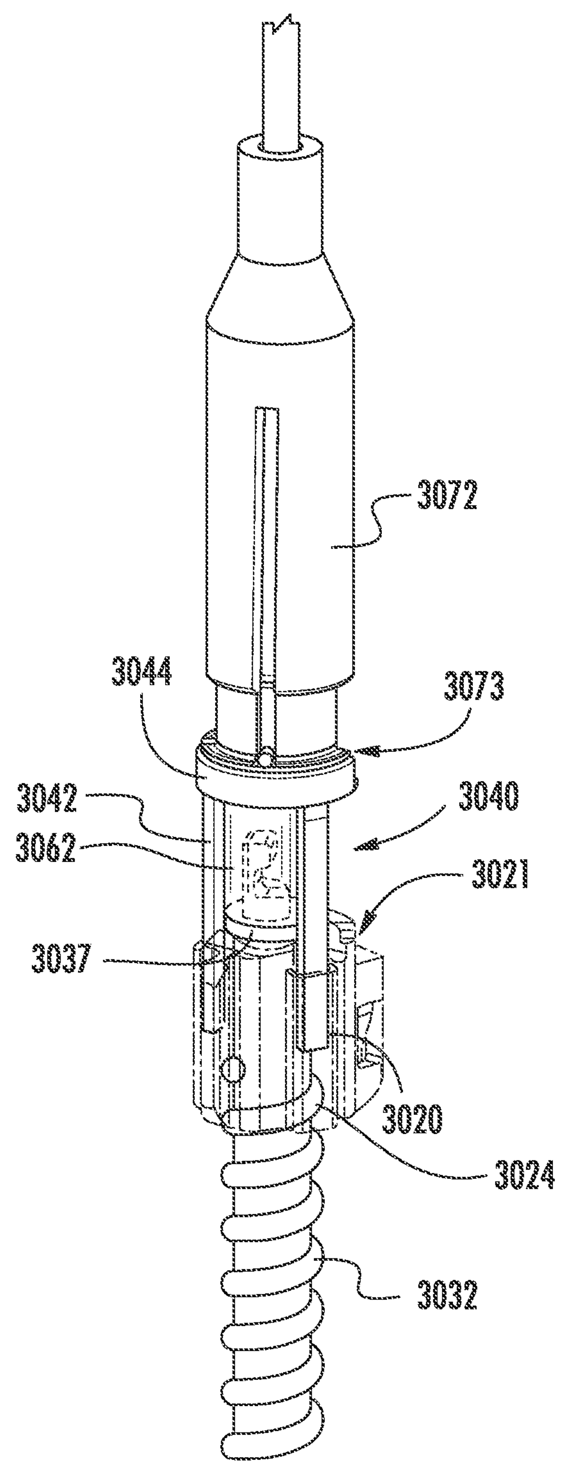
FIG. 11A is a perspective view similar to FIG. 9, but showing the helical anchor deployed.
Figure 11B:
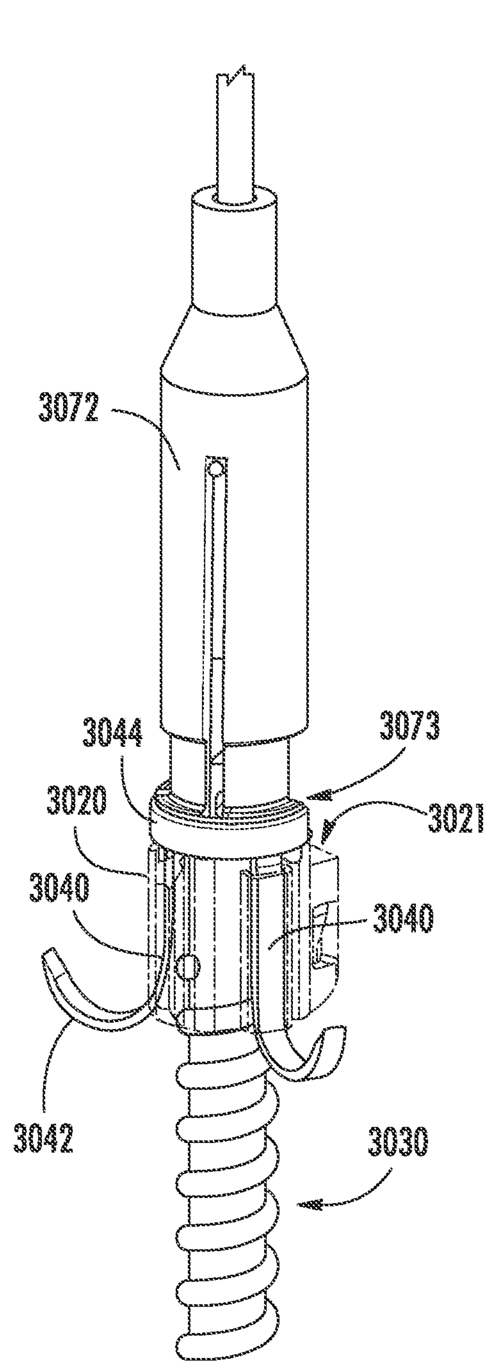
FIG. 11B is a perspective view similar to FIG. 11A, but showing the talons, in addition to the helical anchor, deployed.
Figure 11C:
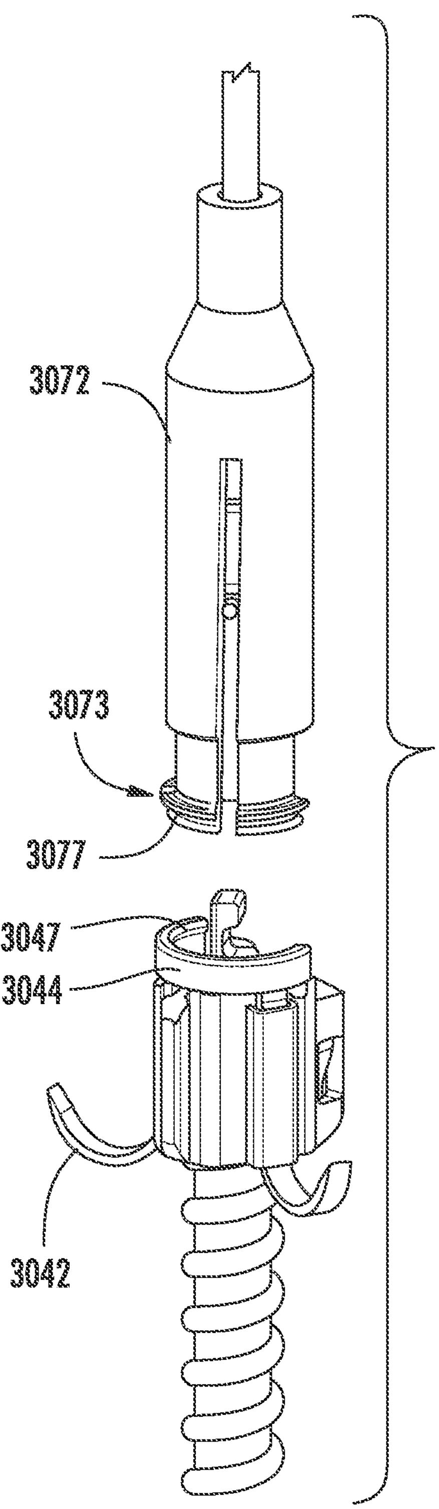
FIG. 11C is a perspective view similar to FIG. 11A and FIG. 11B, but showing deployment elements being withdrawn after deployment of the anchor assembly.

An example of a manner in which the embodiment of an anchor drive mechanism 3060 illustrated in FIGS. 9 and 10 actuates the two or more anchors of the anchor assembly 3010 may be appreciated with reference to FIGS. 11A-11C. In an unadvanced (e.g., delivery) position, as illustrated in FIGS. 9 and 10, a distal helical portion 3032 (shown as a helical threaded portion, but which may be configured as a helical coil, as in the embodiments of FIGS. 4 and 5) of the helical anchor 3030 is seated within threads 3024 in the anchor housing 3020. Accordingly, rotation of the anchor cover 3062 (via rotation of the talon pusher 3072, such as via rotation of the flexible elongate member 3064) causes the helical anchor 3030 to rotationally advance distally, as illustrated in FIG. 11A. The talon pusher 3072 rotates relative to the talon collar 3044 yet may remain substantially in its initial axial position (not axially advanced as the helical anchor 3030 is advanced), so as not to axially advance the talon anchor 3040). The anchor cover 3062 thus distally advances with the helical anchor 3030 (with the projection 3035 moving distally along the slot 3075), relative to the talon pusher 3072, and may advance distally from within the talon pusher 3072 to a position distally outside the talon pusher 3072. The helical anchor 3030 may be distally advanced into the tissue until the proximal-most turn of the helical portion 3032 is positioned within an unthreaded distal section 3026 in the anchor bore 3023 of the anchor housing 3020, such as shown in FIG. 11B (with the anchor housing 3020 shown in phantom). Further rotation of the helical anchor 3030 within the anchor housing 3020, as well as inhibition of proximal axial movement of the helical anchor 3030 are substantially as in the embodiment of FIGS. 6A-6D, reference thus being made thereto for the sake of brevity and without intent to limit. Distal axial movement of the helical anchor 3030 relative to the anchor housing 3020 may be inhibited by engagement of an anchor head shoulder 3037 (such term being used for the sake of convenience, without intent to limit, and may be used interchangeably herein with flange or projection or the like) with a proximal end 3021 of the anchor housing 3020.

As illustrated in FIG. 11B, once the helical anchor 3030 has been advanced as far as desired, the talon pusher 3072 may be axially advanced in a distal direction to advance the tines 3042 of the talon anchor 3040 to the desired extent. In the embodiment illustrated in FIG. 11B, the tines 3042 curve radially outwardly from the longitudinal axis LA of the anchor assembly 3010. In some embodiments, depending on relative dimensions and positions of the talon pusher 3072 and the anchor cover 3062, the anchor cover 3062 may proximally extend within the talon pusher 3072, as illustrated. It will be appreciated that the talon pusher 3072 may advance distally axially even if the anchor cover 1062 has not been advanced distally (such as upon distally advancing the helical coil 3032).

Once the helical anchor 3030 and talon anchor 3040 are deployed as desired, the distal end 3073 of the talon pusher 3072 may be disengaged from the talon collar 3044 (e.g., by flexing inwardly if positioned within the talon collar 3044 or by flexing outwardly if positioned over the talon collar 3044) to release the anchor drive mechanism 3060 from the anchor assembly 3010. The talon pusher 3072 and anchor cover 3062 may be proximally withdrawn, as illustrated in FIG. 11C.

It will be appreciated that various modifications may be made to the configurations of the anchors described herein. For instance, the embodiment of FIGS. 3 and 4 shows two tines 1042 whereas more than one tine may be provided on a talon anchor, such as illustrated in the talon anchor 2040 of FIG. 6, having three tines 2042. The spacing of the two or more tines may be varied, such as equidistant or otherwise. It will further be appreciated that a talon anchor with a single tine may be provided in an anchor assembly formed in accordance with principles of the present disclosure. Further variations to anchor assemblies and anchor elements, as well as selections of materials thereof, may be made such as disclosed in U.S. patent application Ser. No. 17/108,512, filed Dec. 1, 2020, and titled *Coil And Barb Anchors For Heart Valve Repair Devices,* which application is hereby incorporated by reference herein in its entirety for all purposes.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases “at least one”, “one or more”, and “and/or”, as used herein, are open-ended expressions that are both conjunctive and disjunctive in operation. The terms “a”, “an”, “the”, “first”, “second”, etc., do not preclude a plurality. For example, the term “a” or “an” entity, as used herein, refers to one or more of that entity. As such, the terms “a” (or “an”), “one or more” and “at least one” can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader’s understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term “comprises/comprising” does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms “a”, “an”, “the”, “first”, “second”, etc., do not preclude a plurality. Reference signs in the claims are provided merely as a clarifying example and shall not be construed as limiting the scope of the claims in any way.

What is claimed is:

1. An anchor system configured to secure an implantable device within a body, the anchor system comprising:

an anchor assembly comprising a first anchor element and a second anchor element;

an anchor drive mechanism;

a first actuator configured to engage the first anchor element to move the first anchor element independently of the second anchor element; and a second actuator configured to engage the second anchor element, and engageable with the first actuator to allow the first actuator to move relative to the second actuator to move the first anchor element independently of the second anchor element, and to move together with the first actuator, while engaged with the first actuator, to move the second anchor element independently of the first anchor element.

2. The anchor system of claim 1, wherein the first actuator and the second actuator respectively move the first anchor element and the second anchor element by different actuation movements.

3. The anchor system of claim 2, wherein the first actuator rotationally moves the first anchor element.

4. The anchor system of claim 3, wherein the second actuator axially moves the second anchor element.

5. The anchor system of claim 1, wherein the first actuator distally advances the first anchor element relative to the second anchor element while the first actuator is engaged with the second actuator.

6. The anchor system of claim 1, wherein the first actuator and the second actuator are engageable to allow relative rotation therebetween.

7. The anchor system of claim 6, wherein the first actuator is rotationally movable relative to the second actuator while engaged therewith to move the first anchor element to engage tissue.

8. The anchor system of claim 1, wherein the first actuator is rotationally movable into and out of engagement with the second actuator.

9. The anchor system of claim 1, wherein the first actuator and the second actuator are engageable to be axially movable together to axially advance the second anchor element.

10. The anchor system of claim 1, wherein the anchor drive mechanism further comprises a flexible elongate member with the first actuator provided at a distal end of the flexible elongate member.

11. The anchor system of claim 1, wherein the first anchor element is a rotatably advanced helical anchor and the second anchor element is an axially advanced talon anchor.

12. The anchor system of claim 11, wherein the first actuator is an anchor cover configured to be coupled with an anchor head of the helical anchor, and the second actuator is a talon collar configured to be operatively engaged with the talon anchor.

13. The anchor system of claim 12, wherein the anchor cover is rotatable relative to the talon collar to axially advance the helical anchor relative to the talon anchor, and is rotatable into engagement with the talon collar to axially advance the talon collar and the talon anchor.

14. An implantable device comprising:

a frame;

an anchor assembly mounted on the frame and comprising a first anchor element and a second anchor element;

an anchor drive mechanism;

a first actuator portion configured to engage the first anchor element; and a second actuator portion configured to engage the second anchor element and the first actuator portion, and mounted to move together with the first actuator portion to move the second anchor element independently of the first anchor element while the second actuator portion is engaged with the first actuator portion, and to allow the first actuator portion to move the first anchor element independently of the second anchor element.

15. The implantable device of claim 14, wherein the first actuator portion and the second actuator portion respectively move the first anchor element and the second anchor element by different actuation movements.

16. The implantable device of claim 14, wherein the first actuator portion and the second actuator portion are formed on different portions of an anchor cover coupled to the anchor drive mechanism and configured to extend over a proximal portion of the first anchor element.

17. The implantable device of claim 16, wherein the second actuator portion is rotatable into and out of engagement with a portion of the second anchor element.

* * * * *